United States Patent
Imhof et al.

(10) Patent No.: US 10,434,254 B2
(45) Date of Patent: Oct. 8, 2019

(54) METHOD FOR CONFIGURING AN INSULIN PUMP WITH CONFIGURING DEVICE

(71) Applicants: Roche Diagnostics International AG, Rotkreuz (CH); Roche Diagnostics Operations, Inc., Indianapolis, IN (US)

(72) Inventors: Erich Imhof, Utzenstorf (CH); Guido Konrad, Bern (CH); James R. Long, Fishers, IN (US); Phillip E. Pash, Indianapolis, IN (US); Robert E. Reinke, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 767 days.

(21) Appl. No.: 13/726,992

(22) Filed: Dec. 26, 2012

(65) Prior Publication Data

US 2014/0180241 A1 Jun. 26, 2014

(51) Int. Cl.
*G06Q 50/00* (2012.01)
*A61M 5/172* (2006.01)
(Continued)

(52) U.S. Cl.
CPC ....... *A61M 5/1723* (2013.01); *G06F 19/3468* (2013.01); *G06F 21/6218* (2013.01); *G06F 2221/2149* (2013.01)

(58) Field of Classification Search
CPC ........ G06Q 50/22; G06Q 50/24; G06Q 40/08; G06Q 10/10; G06F 19/322; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; A61N 1/08; G16H 10/00; G16H 10/20; G16H 10/40; G16H 10/60;
(Continued)

(56) References Cited

U.S. PATENT DOCUMENTS 4,898,578 A * 2/1990 Rubalcaba, Jr. ...... A61M 5/172
128/DIG. 13
8,118,770 B2 2/2012 Galley et al.
(Continued)

*Primary Examiner* — Tran N Nguyen
(74) *Attorney, Agent, or Firm* — Harness Dickey

(57) ABSTRACT

An insulin pump is configurable by a configurator. The pump has parameter blocks, each with a respective parameter and an associated restriction setting, and the configurator has an authorization level. Configuring the pump includes receiving, by the configurator, a request to access a parameter on the pump. The method also includes identifying, by the configurator, the parameter block that includes the parameter. Moreover, the method includes retrieving, by the configurator from the pump, the parameter and the associated restriction setting, and comparing, by the configurator, the authorization level of the configurator to the restriction setting. Also, the method includes determining, by the configurator, whether the configurator is authorized to write to the parameter block based on the comparison. Additionally, the method includes writing, by the configurator, to the parameter block on the insulin pump in response to a determination that the configurator is authorized to write to the parameter block.

19 Claims, 7 Drawing Sheets

| | 1 12<br>Auth. 1<br>Pump | 2 19<br>Auth. 2<br>Meter | 3 17a<br>Auth. 3<br>PC #1 | 4 17b<br>Auth. 4<br>PC #2 |
|---|---|---|---|---|
| 21a→ Ⓐ Block 1<br>Parameter W<br>Restriction A | Read/write | Read/write | Read/write | Read/write |
| 21b→ Ⓑ Block 2<br>Parameter X<br>Restriction B | Read | Read/write | Read/write | Read/write |
| 21c→ Ⓒ Block 3<br>Parameter Y<br>Restriction C | Read | Read | Read/write | Read/write |
| 21d→ Ⓓ Block 4<br>Parameter Z<br>Restriction D | Read | Read | Read | Read/write |

(51) Int. Cl.
  *G06F 19/00* (2018.01)
  *G06F 21/62* (2013.01)
  *G06Q 10/00* (2012.01)

(58) Field of Classification Search
  CPC ........ G16H 10/65; G16H 15/00; G16H 20/00;
  G16H 20/10; G16H 20/13; G16H 20/17;
  G16H 20/30; G16H 20/40; G16H 20/60;
  G16H 20/70; G16H 20/90; G16H 30/00;
  G16H 30/20; G16H 30/40; G16H 40/00;
  G16H 40/20; G16H 40/40; G16H 40/60;
  G16H 40/63; G16H 40/67; G16H 50/00;
  G16H 50/20; G16H 50/30; G16H 50/50;
  G16H 50/70; G16H 50/80; G16H 70/00;
  G16H 70/20; G16H 70/14; G16H 70/60;
  G16H 80/00
  See application file for complete search history.

(56) References Cited

U.S. PATENT DOCUMENTS

| | | |
|---|---|---|
| 2004/0030323 A1* | 2/2004 | Ullestad ............ A61M 5/14276 604/891.1 |
| 2008/0103447 A1* | 5/2008 | Reggiardo ........ A61M 5/14244 604/131 |
| 2008/0104393 A1 | 5/2008 | Glasser et al. |
| 2009/0270810 A1 | 10/2009 | DeBelser et al. |
| 2010/0036845 A1 | 2/2010 | Godfrey et al. |
| 2010/0160860 A1 | 6/2010 | Celentano et al. |

* cited by examiner

|  | [1] 12 Auth. 1 Pump | [2] 19 Auth. 2 Meter | [3] 17a Auth. 3 PC #1 | [4] 17b Auth. 4 PC #2 |
|---|---|---|---|---|
| 21a Ⓐ Block 1 Parameter W Restriction A | Read/write | Read/write | Read/write | Read/write |
| 21b Ⓑ Block 2 Parameter X Restriction B | Read | Read/write | Read/write | Read/write |
| 21c Ⓒ Block 3 Parameter Y Restriction C | Read | Read | Read/write | Read/write |
| 21d Ⓓ Block 4 Parameter Z Restriction D | Read | Read | Read | Read/write |

FIG. 4

METHOD FOR CONFIGURING AN INSULIN PUMP WITH CONFIGURING DEVICE

FIELD

The present disclosure relates to an insulin pump and, more particularly, relates to a method for configuring an insulin pump using a configuring device.

BACKGROUND

Diabetes mellitus, often referred to as diabetes, is a chronic condition in which a person has elevated blood glucose levels that result from defects in the body's ability to produce and/or use insulin. Diabetes can be treated by injecting predetermined dosages of insulin to the patient to control the level of glucose in the bloodstream. For instance, some diabetes patients rely on an insulin pump to deliver the predetermined dosages to the patient.

The insulin pump can closely imitate a normally functioning pancreas by releasing multiple small doses of insulin each day into the body through an infusion set to regulate blood glucose levels. The dosage delivery rate of these small doses (i.e., the basal rate) can vary from user to user. Also, even for a particular user, the basal rate can change throughout the day, and the basal rate can depend upon various factors (e.g., the user's metabolism, physical health, stress levels, amount of exercise, etc.).

Insulin pumps can also deliver (either automatically or selectively) bolus doses of insulin. These bolus doses can be delivered before meals or snacks to compensate for the caloric intake. Also, bolus dosages can be delivered to correct high blood glucose levels. Moreover, the pump can be configured to deliver multiple types of bolus dosages (e.g., a "standard bolus," an "extended bolus," a "combination bolus/multiwave bolus," or other type). These dosages can be adjusted according to the patient's particular physiology, eating habits, etc.

In some cases, the insulin pump can include a display and buttons or other input devices for inputting commands and other entries for configuring the pump. Also, in some cases, a separate device can be used to configure the pump. For instance, the patient's doctor can use a personal computer to configure the pump to include basal dosage profiles, maximum bolus dosage limits, etc. that are tailored for the particular patient. Moreover, in some embodiments, a blood glucose meter or other device can be used to select between predetermined temporary basal dosage rates that are saved on the pump.

SUMMARY

This section provides a general summary of the disclosure, and is not a comprehensive disclosure of its full scope or all of its features.

In order to ensure that the pump is properly configured, a computer-implemented method of configuring an insulin pump using a pump configuring device is disclosed. The insulin pump has a plurality of parameter blocks, and each of the plurality of parameter blocks has a respective parameter and an associated restriction setting (i.e., access tag). The pump configuring device has a predetermined authorization level. The method includes receiving, by the pump configuring device, a request to access one of the parameters on the insulin pump. The method also includes identifying, by the pump configuring device, the one of the plurality of parameter blocks that includes the one of the parameters. Moreover, the method includes retrieving, by the pump configuring device from the insulin pump, the one of the parameters and the restriction setting associated with the one of the parameters. Furthermore, the method includes comparing, by the pump configuring device, the authorization level of the pump configuring device to the restriction setting associated with the one of the parameters. Also, the method includes determining, by the pump configuring device, whether the pump configuring device is authorized to write to the one of the plurality of parameter blocks based on the comparison of the authorization level and the restriction setting. Additionally, the method includes writing, by the pump configuring device, to the one of the plurality of parameter blocks on the insulin pump in response to a determination that the pump configuring device is authorized to write to the one of the parameter blocks.

In some embodiments, the method further includes displaying, by the pump configuring device, the parameter on a display of the pump configuring device. Displaying the parameter can include displaying the parameter as a changeable parameter in response to the determination that the pump configuring device is authorized to write to one of the parameter blocks. Moreover, the method can include receiving, by the pump configuring device, a request to change the parameter to a new value, wherein writing to the one of the plurality of parameter blocks includes writing the new value of the one of the parameters to the one of the plurality of parameter blocks. The method can additionally include prompting a user of the pump configuring device for confirmation of the request to change the one of the parameters to the new value. Also, displaying the parameter can include displaying the parameter to indicate that the parameter is unchangeable in response to a determination that the pump configuring device is unauthorized to write to the one of the parameter blocks. Still further, identifying the one of the plurality of parameter blocks that includes the one of the parameter can include requesting, by the pump configuring device from the insulin pump, a location of the one of the plurality of parameter blocks on the insulin pump and receiving, from the insulin pump to the pump configuring device, the location of the one of the plurality of parameter blocks on the insulin pump. Furthermore, the pump configuring device can be one of a first pump configuring device and a second pump configuring device, wherein the first pump configuring device has a first authorization level and the second pump configuring device has a second authorization level, and wherein the second authorization level authorizes writing to more of the plurality of parameter blocks than the first authorization level. Additionally, the first pump configuring device can be a blood glucose meter and the second pump configuring device can be a personal computer that runs pump configuring software. Moreover, the pump configuring device can be usable by a first user and can be separately useable by a second user, wherein the predetermined authorization level of the pump configuring device remains the same for the first user and the second user. Furthermore, the plurality of parameter blocks can include a plurality of active parameter blocks and a plurality of backup parameter blocks, wherein each of the active parameter blocks has a corresponding backup parameter block, wherein writing to the one of the plurality of parameter blocks includes writing a new parameter to the one of the backup parameter blocks and subsequently writing the new parameter to the active parameter block corresponding to the one of the backup parameter blocks. The method can further include determining the new parameter on the one of the backup parameter blocks is valid before writing the new parameter to the active parameter block, and restoring an old parameter to the one of the backup parameter blocks as a result of determining that the new parameter is invalid. Additionally, writing to the one of the plurality of parameter blocks can include writing to at least two parameter blocks in succession.

In addition, a pump configuring device is disclosed that is operable to configure an insulin pump having a plurality of parameter blocks. Each of the plurality of parameter blocks has a respective parameter and an associated restriction setting. The insulin pump configuring device includes an input device that is operable to receive a request to access one of the parameters on the insulin pump. The device also includes a memory device with a predetermined authorization level of the pump configuring device saved thereon. The device further includes a communication device that is operable to communicate with the insulin pump to retrieve the one of the parameters and the restriction setting associated with the one of the parameters. Additionally, the device includes a processor that is operable to compare the authorization level of the pump configuring device to the restriction setting associated with the one of the parameters, determine whether the pump configuring device is authorized to write to the one of the plurality of parameter blocks based on the comparison of the authorization level and the restriction setting, and write to the one of the plurality of parameter blocks on the insulin pump in response to a determination that the pump configuring device is authorized to write to the one of the parameter blocks.

Furthermore, a diabetes treatment system is disclosed that includes an insulin pump having a plurality of parameter blocks. Each of the plurality of parameter blocks has a respective parameter and an associated restriction setting. The system also includes an insulin pump configuring device that includes an input device that is operable to receive a request to access one of the parameters on the insulin pump. The configuring device also includes a memory device with a predetermined authorization level of the pump configuring device saved thereon. Also, the configuring device includes a communication device that is operable to communicate with the insulin pump to retrieve the one of the parameters and the restriction setting associated with the one of the parameters. Moreover, the configuring device includes a processor that is operable to compare the authorization level of the pump configuring device to the restriction setting associated with the one of the parameters, determine whether the pump configuring device is authorized to write to the one of the plurality of parameter blocks based on the comparison of the authorization level and the restriction setting, and write to the one of the plurality of parameter blocks on the insulin pump in response to a determination that the pump configuring device is authorized to write to the one of the parameter blocks.

Moreover, a computer-implemented method of configuring an insulin pump using a pump configuring device is disclosed. The insulin pump has a plurality of parameter blocks, and each of the plurality of parameter blocks have a respective old parameter and an associated restriction setting. The plurality of parameter blocks are also divided into a plurality of active parameter blocks and a plurality of backup parameter blocks. Each of the active parameter blocks are substantially copied by a corresponding backup parameter block. The pump configuring device also has a predetermined authorization level. The method includes receiving, by the pump configuring device, a request to change one of the old parameters on the insulin pump to a new parameter. The method also includes identifying, by the pump configuring device, the one of the plurality of active parameter blocks and the one of the plurality of backup parameter blocks that includes the one of the old parameters. Moreover, the method includes retrieving, by the pump configuring device from the insulin pump, the one of the old parameters and the restriction setting associated with the one of the old parameters. Furthermore, the method includes comparing, by the pump configuring device, the authorization level of the pump configuring device to the restriction setting associated with the one of the old parameters. Also, the method includes determining, by the pump configuring device, whether the pump configuring device is authorized to write to the one of the plurality of backup parameter blocks based on the comparison of the authorization level and the restriction setting. The method additionally includes overwriting, by the pump configuring device, the one of the old parameters with the new parameter on the one of the plurality of backup parameter blocks in response to a determination that the pump configuring device is authorized to write to the one of the backup parameter blocks. Moreover, the method includes determining, by the insulin pump, whether the new parameter is valid after overwriting the one of the old parameters with the new parameter. Furthermore, the method includes overwriting, by the insulin pump, the one of the old parameters with the new parameter on the one of the one of the active parameter blocks that is a substantial copy of the one of the plurality of backup parameter blocks in response to a determination that the new parameter is valid and overwriting, by the insulin pump, the new parameter with the one of the old parameters on the one of the plurality of backup parameter blocks in response to a determination that the new parameter is invalid.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 4 is a chart illustrating relationships between restriction settings for different parameters on the pump and authorization levels for accessing and changing the parameters by a pump configuring device;

Corresponding reference numerals indicate corresponding parts throughout the several views of the drawings.

DETAILED DESCRIPTION

Example embodiments will now be described more fully with reference to the accompanying drawings.

Figure 1A:
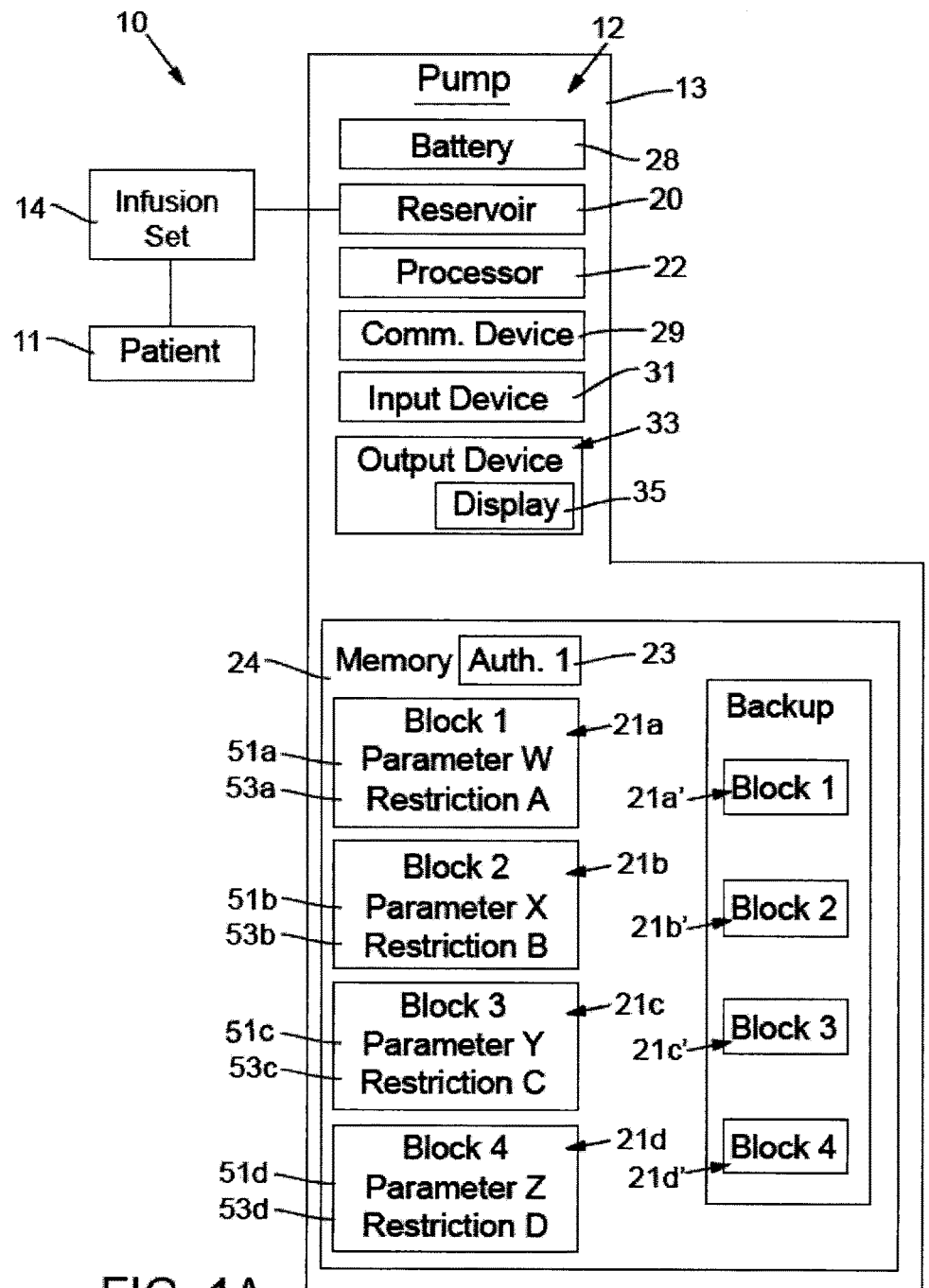
FIGS. 1A and 1B are schematic illustrations of a system for treating diabetes according to exemplary embodiments of the present disclosure.
Figure 1B:
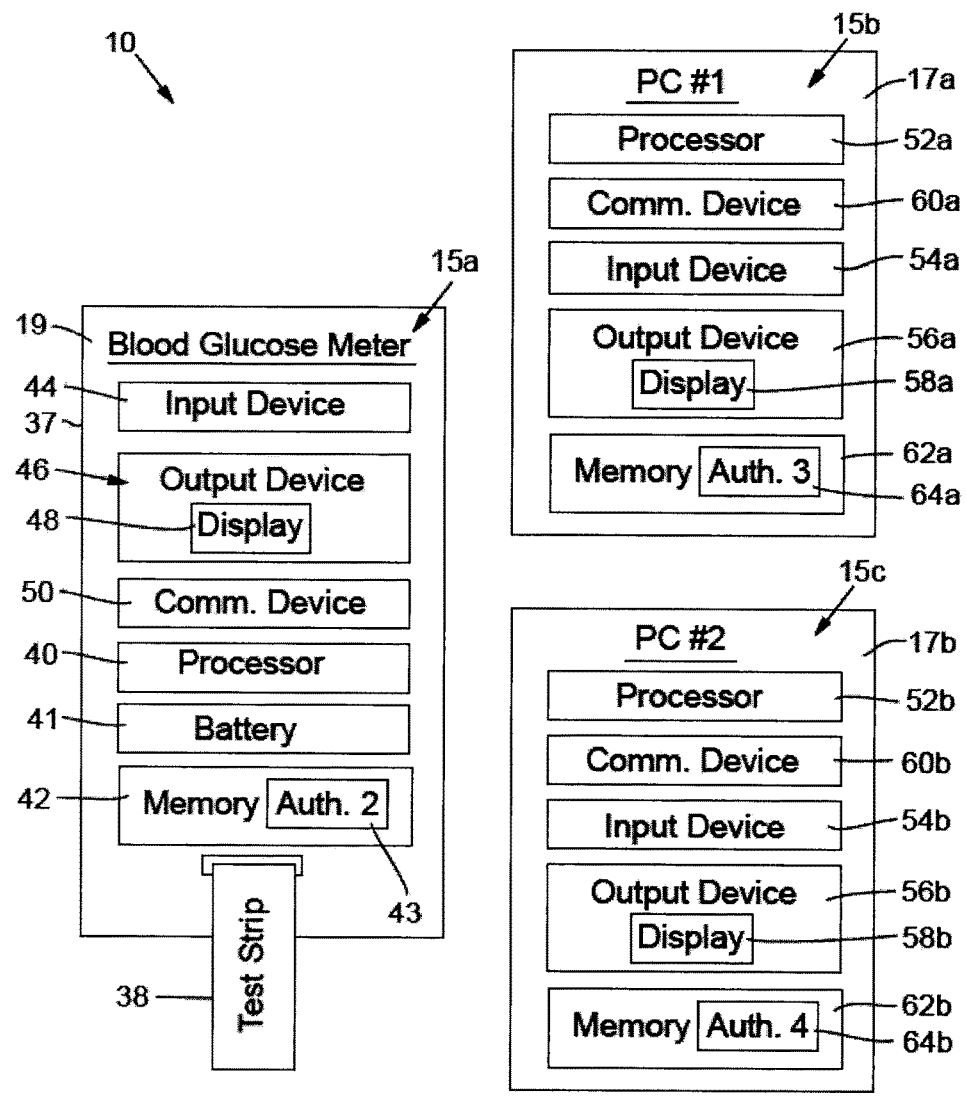
Figure 2:
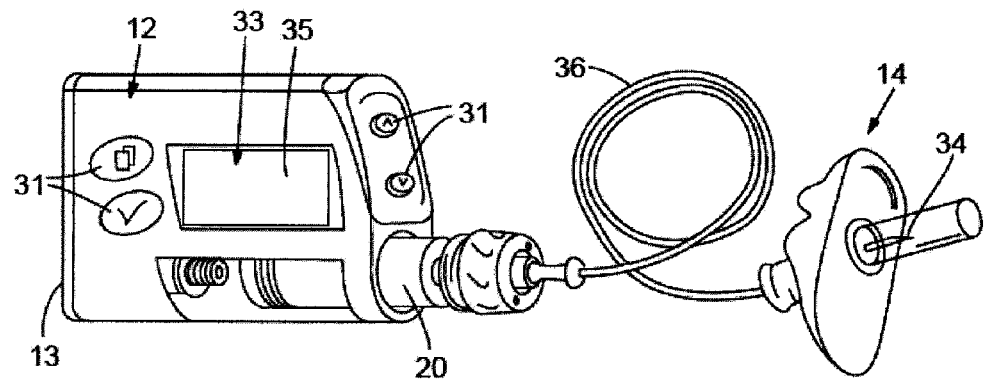
FIG. 2 is perspective view of an insulin pump and an infusion set of the system of FIGS. 1A and 1B.

Referring initially to FIGS. 1A and 1B, a system 10 for treating diabetes is illustrated schematically. As shown, the system 10 can generally include an insulin pump 12 and an infusion set 14 (FIG. 1A), which are operable for delivering controlled dosages of insulin to a patient 11 as will be discussed. Exemplary embodiments of the insulin pump 12 and infusion set 14 are illustrated in FIG. 2. The system 10 can also include one or more pump configuring devices 15a, 15b, 15c (FIG. 1B), which are individually operable to configure the pump 12 (i.e., by changing parameters that govern the operation of the pump 12).

The pump 12 can be configured in a number of ways. Some configurations are patient-specific (e.g., maximum bolus dosage limits, basal dosage profiles, temporary basal rates, etc.) such that the pump 12 operates according to the specific diet, lifestyle, physiology, etc. of the particular patient 11. Other configurations are appropriate for many users (e.g., languages displayed on the graphic user interface of the pump 12, etc.).

As will be discussed below, the system 10 is designed such that certain pump configuring devices 15a, 15b, 15c are authorized to reconfigure the pump 12 (i.e., by adding, deleting, or changing certain parameters stored on the pump 12) while other devices 15a, 15b, 15c are unauthorized to do so. As a result, the pump 12 can be configured in a controlled and efficient manner.

The System

Referring to FIGS. 1A and 2, the insulin pump 12 can incorporate various features of a known, wearable, and portable insulin pump 12. Thus, the insulin pump 12 can include a housing 13 that supports at least one refillable reservoir 20 (i.e., insulin cartridge) containing insulin. (The reservoir 20 is shown partially removed from the housing 13 in FIG. 2.) The reservoir 20 can selectively deliver insulin to the infusion set 14 as will be described in greater detail below.

The pump 12 can also include a processor 22 (i.e., controller) that includes programmed logic and/or other elements for controlling the start and stoppage of insulin delivery from the reservoir 20, the flow rate of the insulin, etc. The pump 12 can additionally include one or more memory devices 24 (FIG. 1A). The memory device 24 can store application programs and data and can be constructed of any suitable combination of volatile and/or nonvolatile memory.

Some or all of the data stored on the memory device 24 can be organized into distinct parameter blocks 21a, 21b, 21c, 21d (i.e., configuration blocks). Each of the individual parameter blocks 21a-21d include a respective parameter Ma, 51b, 51c, 51d (i.e., variable). The parameters 51a-51d are labeled "Parameter W," "Parameter X," "Parameter Y," and "Parameter Z," respectively, in FIG. 1A. The parameters 51a, 51b, 51c, 51d can be of any type, such as a maximum bolus insulin dosage, a basal insulin dosage profile, a temporary basal insulin dosage rate, settings for the languages displayed by the pump 12, or other types of parameters. Each of the parameter blocks 21a-21d can also include an associated restriction setting 53a, 53b, 53c, 53d (i.e., access tag). The restriction settings 53a-53d are labeled "Restriction A," "Restriction B," "Restriction C," and "Restriction D," respectively, in FIG. 1A. As will be discussed, the different restriction settings 53a-53d can be used for regulating whether the pump 12 and/or any of the pump configuring devices 15a, 15b, 15c is allowed to add, delete, or otherwise change the respective parameters 51a-51d in the respective parameter block 21a-21d.

It will be appreciated that the pump 12 can include any number of parameter blocks 21a-21d. Also, each block 21a-21d can include any number of respective parameters 51a-51d.

Moreover, as shown in FIG. 1A, the memory device 24 can further include backup parameter blocks 21a', 21b', 21c', 21d'. The backup parameter blocks 21a', 21b', 21c', 21d' can substantially copy respective ones of the parameter blocks 21a, 21b, 21c, 21d. As such, the backup parameter blocks 21a', 21b', 21c', 21d' each contain the same respective parameters 51a-51d and restriction settings 53a-53d contained in the corresponding parameter block 21a, 21b, 21c, 21d. As will be discussed, the parameter blocks 21a-21d (i.e., the "active parameter blocks") can be relied upon for governing operations of the pump 12 while the backup parameter blocks 21a'-21d' can serve as a backup copy. As will be discussed, however, when the pump 12 is being configured (i.e., changes are made to the parameters 51a-51d), the changes can be written to the backup parameter blocks 21a'-21d' instead of the "active" parameter blocks 21a-21d. Then, assuming that the configuration is valid, the updated contents of the backup parameter blocks 21a'-21d' can be copied to the "active" parameter blocks 21a-21d.

The memory device 24 of the pump 12 can further store a pump authorization level 23 (labeled "Auth. 1" in FIG. 1A) thereon. As will be discussed, the pump authorization level 23 can be used for determining whether the pump 12 is authorized to change or otherwise configure the parameters 51a-51d contained in the parameter blocks 21a-21d.

Moreover, the pump 12 can include a power source, such as a battery 28, for providing power to the components of the pump 12. The battery 28 can include a main battery that supplies power for normal operations of the pump 12, and the battery 28 can include a backup battery that supplies power for only essential operations of the pump 12 when the main battery fails. It will be appreciated that the pump 12 can include additional or alternative power sources (e.g., one or more capacitors, etc.) without departing from the scope of the present disclosure.

Additionally, the pump 12 can include one or more input devices 31 that can be used by the patient 11 for inputting commands directly to the pump 12. As shown in FIG. 2, the input devices 31 can include one or more buttons that the patient 11 can depress for inputting such commands; however, the input device 31 could include a touch-sensitive surface, a sliding switch, or other input device. The pump 12 can further include one or more output devices 33 that can output one or more messages (e.g., messages relating to dosages, etc.). In the embodiments of FIG. 2, the output device 33 includes a display screen 35 for outputting the messages visually; however, the output device 33 could include a speaker for outputting the messages aurally. Moreover, in some embodiments, the output device 33 can include a tactile, vibrating motor for outputting the messages in a tactile manner.

The pump 12 can further include a communications device 29. The communication device 29 can establish communications between the pump 12 and the pump configuring devices 15a-15c as will be discussed in detail below. The communications device 29 can include a wireless transceiver (e.g., BLUETOOTH™ transceiver, etc.), and/or the communications device 29 can include a connector for connecting a wire between the pump 12 and the pump configuring devices 15a-15c.

Furthermore, the infusion set 14 can be of a known type. As shown in FIG. 2, the infusion set 14 can include a cannula 34 that is inserted subcutaneously into the patient 11 (i.e., the user, the person with diabetes, etc.). The infusion set 14 can also include a tube 36 that fluidly connects the cannula 34 to the reservoir 20 of the pump 12. As such, insulin can be delivered from the reservoir 20 and into the patient's bloodstream via the infusion set 14.

Figure 3:
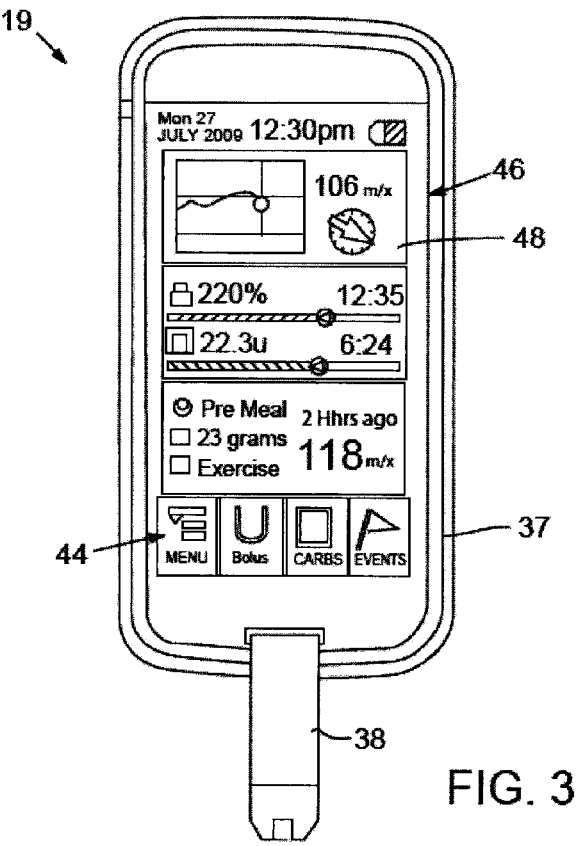
FIG. 3 is a front view of a blood glucose meter of the system of FIGS. 1A and 1B.

Embodiments of the pump configuring devices 15a, 15b, 15c will now be discussed in detail with reference to FIG. 1B. In the embodiments illustrated, the pump configuring device 15a is embodied by a handheld or otherwise portable blood glucose meter 19, which is operable to detect a glucose level in the user's blood. (Exemplary embodiments of the blood glucose meter 19 are illustrated in FIG. 3.) Also, in the embodiments illustrated in FIG. 1B, the other pump configuring devices 15b, 15c are embodied by a first personal computers 17a and a second personal computer 17b, respectively. Both of the computers 17a, 17b are operable to run software for configuring the pump 12 (i.e., pump configuring software). The personal computers 17a, 17b can each be embodied by a desktop computer, laptop computer, personal data assistant (PDA), tablet-type computing device, or other comparable type.

It will be appreciated that the system 10 can include any number of pump configuring devices 15a, 15b, 15c. It will also be appreciated that the devices 15a, 15b, 15c can be embodied by any type of computerized device that is able to communicate with the pump 12 for configuring the pump 12.

Referring now to FIGS. 1B and 3, embodiments of the blood glucose meter 19 will be discussed in detail. The blood glucose meter 19 can include a housing 37 that houses the components of the meter 19. As shown in FIG. 1B, the meter 19 can include a processor 40, which can include programmed logic and/or other elements for controlling the meter 19 and for sending commands to the pump 12.

The meter 19 can also include a memory device 42, which can store application programs and data and can be constructed of any suitable combination of volatile and/or nonvolatile memory. The memory device 42 can also include a respective meter authorization level 43 (indicated as "Auth. 2" in FIG. 1B). The meter authorization level 43 can be used for determining whether the meter 19 is authorized to change or otherwise configure certain ones of the parameters 51a-51d on the pump 12 as will be discussed in detail below. The authorization level 43 can be different from the authorization level 23 of the pump 12 (FIG. 1A) such that the meter 19 can be authorized to configure different parameter blocks 21a-21d than the pump 12.

Moreover, the meter 19 can include a battery 41 or other power source that supplies power to the components of the meter 19. Also, the meter 19 can include one or more input devices 44 with which the patient 11 can input commands. The input devices 44 can include buttons, switches, a touch sensitive surface, or any other suitable device. The meter 19 can further include one or more output devices 46 that output information relating to operations of the system 10. The output devices 46 can be of any suitable type, such as a display 48 that outputs information visually, a speaker that outputs audible information, a vibrating motor that outputs tactile information, etc. In the embodiments of FIG. 3, the meter 19 includes the display 48, and the display 48 includes one or more touch-sensitive areas, such that the display 48 can function as both an input device 44 and an output device 46. Also, as shown in FIG. 3, the display 48 can display various information, such as the current date and time, graphical information about insulin dosages, etc. Furthermore, the display 48 can display user selectable options for allowing the patient 11 to enter bolus information (labeled "Bolus" in FIG. 3), carbohydrate information (labeled "Carbs" in FIG. 3), or other information related to meals, exercise, periods of stress, physiological events such as menstruation, etc. (labeled "Events" in FIG. 3).

Also, the meter 19 can be of a known type for detecting the current (i.e., actual) blood glucose level of the patient 11. More specifically, the patient 11 can apply blood to a test strip 38, and the meter 19 can receive the strip 38 and detect the amount of glucose in the blood thereon. This information can be useful for calculating an appropriate bolus dosage or for other purposes. Also, this information can be stored in the memory device 42 in a suitable database for future analysis.

The blood glucose readings can also be associated or otherwise stored with other information in the memory device 42. For instance, the memory device 42 can store the blood glucose readings with other health related information of the particular patient 11. More specifically, the memory device 42 can store recommended bolus and carbohydrate advice history records. The memory device 42 can further store health, carbohydrate, and blood-glucose-related variables (e.g., insulin sensitivities of the patient 11 for particular time segments of particular days of the week, etc.).

The meter 19 can further include a communication device 50, such as a wireless transceiver (e.g., a BLUETOOTH™ transceiver, etc.) or a connector for connecting a wire. Thus, the communication device 50 of the meter 19 can selectively communicate with the communication device 29 of the insulin pump 12 wirelessly and/or via a hardwire connection. As will be discussed, the communication devices 50, 29 can provide two-way communication between the meter 19 and the insulin pump 12.

Thus, the processor 40 can run software stored in the memory device 42. Also, various input commands can be provided from the patient 11 via the input device 44 (e.g., the touch-sensitive surface of the display 48) for performing various functions. For instance, the processor 40 can calculate a recommended meal bolus, a recommended correction bolus, a recommended total bolus, and/or a suggested carbohydrate amount in this manner. Also, the processor 40 can cause the communication device 50 to transmit various control commands to the pump 12. The meter 19 can send a variety of control commands, such as a START BOLUS DELIVERY, STOP PUMP, and other commands. The insulin amount, dosage time, insulin flow rate, etc. can also be specified in this command. Moreover, the meter 19 can be used to read the parameters 51a-51d on the pump 12 and, if the meter 19 is authorized to do so, the meter 19 can be used to write to at least some of the parameter blocks 21a-21d for adding, deleting, and/or changing the respective parameter(s) 51a-51d.

Furthermore, as shown in FIG. 1B, the personal computers 17a, 17b can each include components that are typically included on a personal computer. For instance, the personal computers 17a, 17b can each include respective processors 52a, 52b that are operable for processing data, outputting control commands, etc. Also, the computers 17a, 17b can include one or more input devices Ma, 54b (e.g., keyboard, computer mouse, touch-sensitive surface, etc.). Furthermore, the computers 17a, 17b can include one or more output devices 56a, 56b. The output devices 56a, 56b can be embodied by respective displays 58a, 58b, and/or the output devices 56a, 56b can be embodied otherwise (e.g., by speakers, etc.). Moreover, the computers 17a, 17b can include a respective communication device 60a, 60b, such as a wireless transceiver (e.g., a BLUETOOTH™ transceiver, etc.) or a connector for connecting a wire. Thus, the communication devices 60a, 60b can selectively communicate with the communication device 29 of the insulin pump 12 wirelessly and/or via a hardwire connection. As will be discussed, each communication device 60a, 60b can provide two-way communication between the insulin pump 12 and the respective computer 17a, 17b.

Still further, the personal computers 17a, 17b can each include a memory device 62a, 62b, which can store application programs and data and can be constructed of any suitable combination of volatile and/or nonvolatile memory. The memory devices 62a, 62b can also include a respective computer authorization level 64a, 64b (indicated as "Auth. 3" and "Auth. 4" in FIG. 1B). The computer authorization levels 64a, 64b can be used for determining whether the computer 17a, 17b is authorized to change or otherwise configure certain parameters 51a-51d on the pump 12. The authorization levels 64a, 64b can be different from each other such that each computer 17a, 17b can be authorized to configure different parameter blocks 21a-21d. Also, one or both authorization levels 64a, 64b can be different from the authorization level 43 of the meter 19 such that the computers 17a, 17b can be authorized to configure different parameter blocks 21a-21d than the meter 19 as will be discussed in greater detail below.

Referring now to FIG. 4, a chart is shown that demonstrates whether the pump 12, the meter 19, the first computer 17a, and the second computer 17b are authorized to read and/or write to the parameter blocks 21a-21d. The information and rules set forth in FIG. 4 can be stored on the pump 12, the meter 19, the first computer 17a, and/or the second computer 17b. As shown in FIG. 4, the pump 12 is authorized to write to the parameters in the parameter block 21a. Also, the meter 19 (with its comparatively higher authority of "Auth. 2") is authorized to write to both parameter blocks 21a and 21b. Moreover, the first computer 17a (with its still-higher authority of "Auth. 3") is authorized to write to parameter blocks 21a, 21b, and 21c. Finally, the second computer 17b (with the highest authority) is authorized to write to each of the parameter blocks 21a-21d.

It will be appreciated, then, that the parameters 51a-51d within the parameter blocks 21a-21d can be protected such that only predetermined devices can make changes thereto. For instance, some parameters 51a-51d may have low restriction settings (e.g., those pertaining to fonts displayed on the display 35, etc.) such that the pump 12, meter 19, and computers 17a, 17b can each individually make changes thereto. Other parameters 51a-51d can have high restriction settings (e.g., those pertaining to bolus or basal insulin dosages) such that only some of the pump configuring devices 15a-15c can make changes thereto.

Additionally, in the embodiments illustrated in FIG. 4, each of the pump 12, the meter 19, and the computers 17a-17b is authorized to access (i.e., read) the parameters 51a-51d from the parameter blocks 21a-21d regardless of the respective authorization level 23, 43, 64a, 64b. This can allow the devices to communicate efficiently with each other and to ensure proper operations of the system 10. However, in other embodiments, some parameter blocks 21a-21d can be set to be inaccessible (i.e., unreadable) by any of the pump 12, the meter 19, and/or the computers 17a, 17b.

Furthermore, the system 10 could be arranged considering that the pump 12 is used by the patient 11, but that the meter 19 and/or the computers 17a, 17b are controlled and used by persons other than the patient 11. For instance, the patient 11 can be a child that uses the pump 12, whereas the parent(s) of the child can control and use the meter 19, the patient's doctor can control and use the first computer 17a, and the manufacturer of the pump 12 can control and use the second computer 17b. Thus, the authorization levels 23, 43, 64a, 64b of the pump 12, meter 19, and computers 17a, 17b can be preset with these user/device pairings in mind. For instance, since the child patient 11 wears and operates the pump 12, and the child may not have sufficient knowledge about proper insulin dosages, etc., the pump 12 can have a relatively low authority level 23 such that the pump 12 is only able to make changes to minor parameters 51a-51d (e.g., selections between predetermined temporary basal rates, fonts displayed on the display 35, etc.). In contrast, since the parent may have more knowledge about insulin dosages, etc., the meter 19 can have a higher authority level such that the meter 19 is able to make changes to more parameters 51a-51d (e.g., those changes that are allowed with the pump 12 as well as selections between normal basal rate profiles, etc.). Moreover, since the doctor can have substantial knowledge about the patient's particular medical condition, the first personal computer 17a can have an even higher authority level 64a such that the computer 17a is able to make changes to even more parameters 51a-51d (e.g., those changes that are allowed by the pump 12 and meter 19 as well as defining basal rate profiles, temporary basal rates, maximum bolus dosages, etc.). Finally, the manufacturer will likely need to make overall system changes to the pump 12, the second computer 17b can have the highest authority level 64b such that substantially all of the parameters 51a-51d can be changed therewith. It will also be appreciated that the authority level 23, 43, 64a, 64b of each device can remain the same regardless of the user.

Configuring the Pump Using Pump Configuring Device

Figure 5:
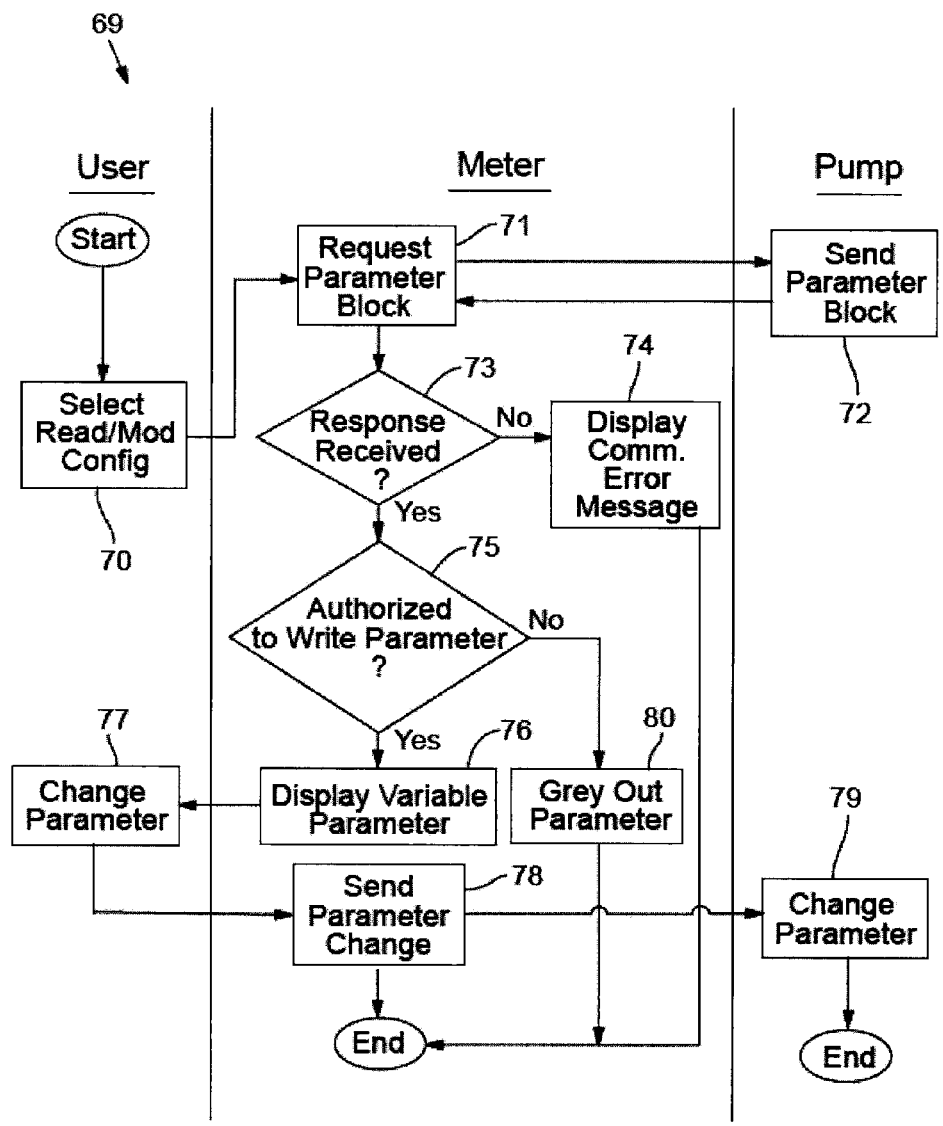
FIG. 5 is a flow chart illustrating a method of configuring an insulin pump using the system of FIGS. 1A and 1B.

Referring now to FIG. 5 exemplary embodiments of a method 69 of configuring the pump 12 will be discussed. For purposes of discussion, the method 69 is illustrated such that the user is attempting to configure the pump 12 using the meter 19. However, the method 69 of FIG. 5 could also apply to scenarios in which the user is attempting to configure the pump 12 using either of the computers 17a, 17b. If the pump 12 is being used for configuring itself, some aspects of the method 69 can apply as will be discussed below; however, the method 69 applies to situations where the separate pump configuring devices 15a, 15b, 15c are being used to configure the pump 12.

The method 69 begins in block 70, wherein the user can navigate through menus and/or other graphical output on the display 48 using the input device 44. Then, the user can select an option to read and/or modify the configuration of the pump 12. Stated differently, the meter 19 can receive a request to access one or more parameters 51a-51d on the pump 12. Block 70 can include a selection to read/modify one parameter 51a-51d, more than one parameters 51a-51d, or each of the parameters 51a-51d on the pump 12.

Then, in block 71, the meter 19 can attempt to identify the parameter block 21a-21d on the pump 12 that includes the parameter(s) 51a-51d specified in block 70. More specifically, the meter 19 can communicate with the pump 12 (via the communication devices 50, 29) and query the pump 12 for the stored location of the parameter block(s) 21a-21d containing the parameter(s) 51a-51d specified in block 70.

Block 72 can include a reply from the pump 12 to the meter 19 identifying the location of the specified parameter block(s) 21a-21d, and the reply can also include the contents of the block(s) 21a-21d (i.e., the respective parameter(s) 51a-51d and restriction setting(s) 53a-53d).

Next, in block 73 the processor 40 of the meter 19 can determine whether the reply of block 72 is complete. If not (block 73 answered negatively), then the display 48 or any other output device 46 can output an error message in block 74. However, if the reply is completely received (block 73 answered affirmatively), then block 75 can follow.

In block 75, the processor 40 can compare the authorization level 43 of the meter 19 to the restriction setting(s) 53a-53d of the parameter block(s) 21a-21d specified in block 70. For instance, the processor 40 can refer to the rules set forth in the chart of FIG. 4 to determine whether the meter 19 is authorized to write to (i.e., configure) the parameter block(s) 21a-21d specified in block 70.

If the processor 40 determines that the meter 19 is unauthorized to write to the parameter block(s) 21a-21d (block 75 answered negatively), then block 80 can follow. In block 80, the display 48 can display the parameter(s) 51a-51d specified in block 70 in a way that indicates that the parameter(s) 51a-51d is/are unchangeable. For instance, the display 48 can "grey out" the parameter(s) 51a-51d (i.e., the parameter(s) 51a-51d can have a different color or otherwise appear different on the display 48 to indicate that the parameter(s) 51a-51d are not modifiable). However, if the meter 19 is authorized to write to the parameter block(s) 21a-21d (block 75 answered affirmatively), then in block 76, the display 48 can display the respective parameter(s) 51a-51d. The display 48 can further prompt the user to input changes to the parameter(s) 51a-51d using the input device 44 of the meter 19.

Next, in block 77, the user can input changes to the parameter(s) 51a-51d using the input device 44. Stated differently, in block 77, the meter 19 receives a request to change the parameter(s) 51a-51d. In some embodiments, the meter 19 can request confirmation from the user of these changes.

Subsequently, in block 78, the meter 19 can send the changes input in block 77 to the pump 12. Finally, in block 79, the processor 22 of the pump 12 can output control commands for writing to the parameter block(s) 21a-21d and changing the parameter(s) 51a-51d therein.

In some embodiments, before overwriting occurs in block 79, the processor 22 of the pump 12 can check that the meter 19 has authority to write to the parameter block(s) 21a-21d to change the parameter(s) 51a-51d therein. Specifically, meter 19 can send its authority level 43 to the pump 12, and the processor 22 can compare the authority level 43 of the meter 19 to the respective restriction setting(s) 53a-53d by referring to the rules of FIG. 4, etc. Assuming that the meter 19 has high enough authority, the pump 12 can overwrite the parameter block(s) 21a-21d in block 78.

Accordingly, the method 69 can ensure that the pump 12 is properly configured. Specifically, the devices 15a, 15b, 15c are able to change certain parameters 51a-51d depending on its preset authority. Therefore, the parameters 51a-51d can be protected against inadvertent changes.

In situations where the pump 12 is used to configure itself, the authority level 23 of the pump 12 can be compared to the restriction setting 53a-53d for the parameters 51a-51d that are specified for change (e.g., similar to block 75). In the rules and information set forth in FIG. 4, the pump 12 has low authority and is allowed to read and write only to parameter block 21a. However, the pump 12 can read each of the parameter blocks 21a-21d.

Figure 6A:
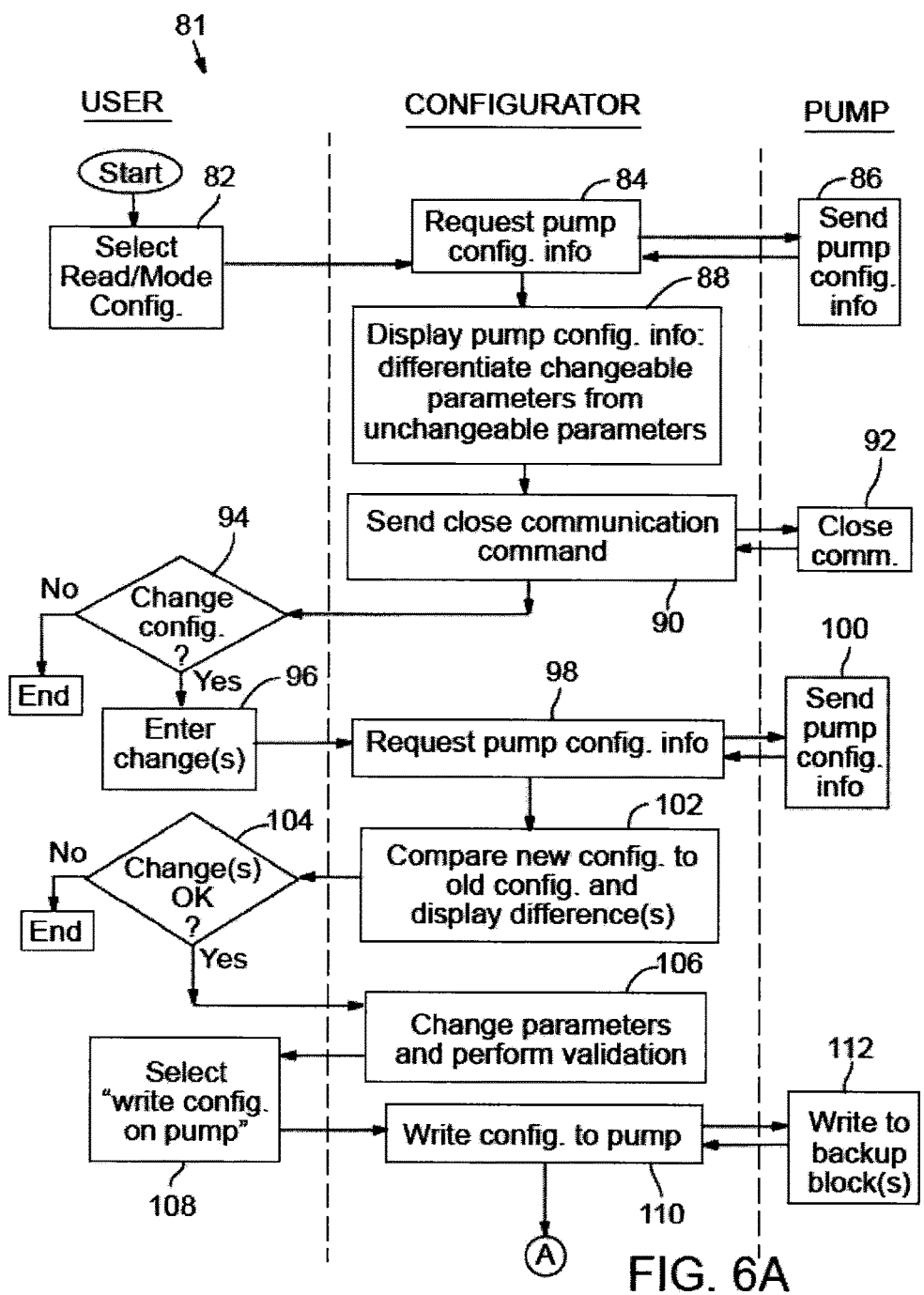
FIGS. 6A and 6B are flow charts illustrating additional embodiments of a method of configuring an insulin pump using the system of FIGS. 1A and 1B.
Figure 6B:
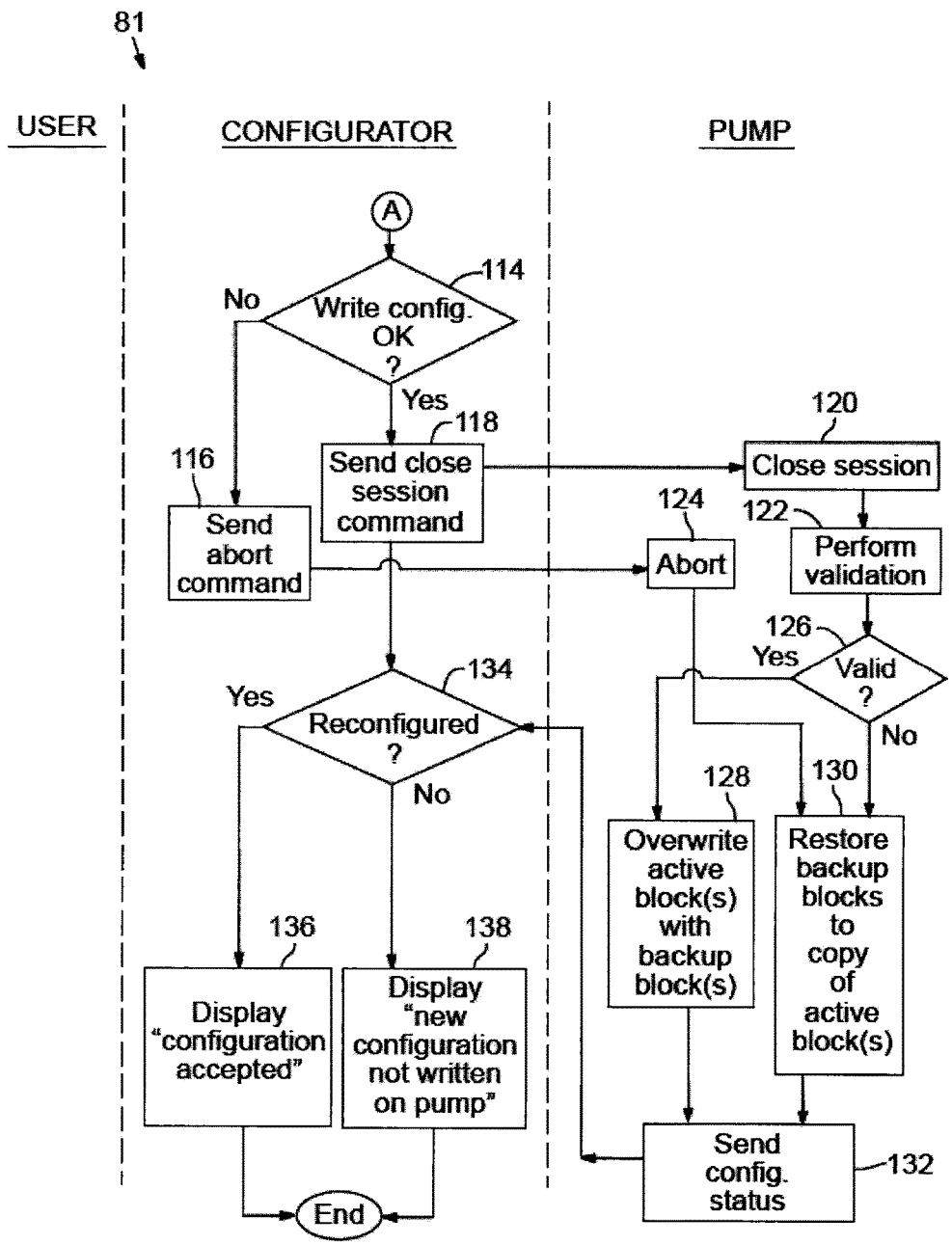

Referring now to FIGS. 6A and 6B, additional embodiments of a method 81 of configuring the pump 12 using one of the pump configuring devices 15a-15c are illustrated. For purposes of discussion, it will be assumed that the second computer 17b is the configuring device; however, the method 81 can equally apply where the meter 19 or first computer 17a is being used for configuring the pump 12.

The method 81 can begin in block 82, wherein the user selects an option to read and/or modify the configuration of the pump 12. This can be a request to read and/or modify specific parameters 51a-51d, or a request to read and/or modify substantially all of the parameters 51a-51d.

Then, in block 84, the computer 17b can communicate with the pump 12 (using the communications devices 29, 60b) and request configuration information from the pump 12. The pump 12 can reply with configuration information in block 86. The configuration information can be the location of the parameter(s) 51a-51d specified in block 82 in the pump's memory device 24, the values for the parameters 51a-51d, the associated restriction settings 53a-53d, etc. This configuration information can be temporarily saved in the memory device 62b of the computer 17b.

Subsequently, in block 88, the display 58b can visually output at least some of the configuration information sent in block 86. In some embodiments of block 88, the display 58b can display the current parameters 51a-51d specified in block 82. Also, the processor 52b can compare the authorization level 64b of the computer 17b to each of the restriction settings 53a-53d sent in block 86 in order to determine whether those parameters 51a-51d are changeable (i.e., configurable) or unchangeable (i.e., unconfigurable) as described above. To demonstrate that parameters 51a-51d are unchangeable, the display 58b can "grey out" the displayed parameter 51a-51d.

Next, in block 90, the computer 17b can send a "close communication" command to the pump 12 via the communication devices 29, 60b. Next, in block 92, the pump 12 can close communications with the computer 17b.

Then, in decision block 94, the user can decide whether to make any changes to the changeable parameters 51a-51d. If the user decides not to make any changes to the parameters 51a-51d (decision block 94 answered negatively), then the method 81 can terminate. However, if the user wishes to make changes (decision block 94 answered affirmatively), then in block 96, the user can enter the desired changes using the input device 54b. Block 98 can follow.

In block 98, the computer 17b can again establish communications with the pump 12, and the computer 17b can again request configuration information from the pump 12 similar to block 84. For instance, the computer 17b can request one or more of the parameters 51a-51d saved in the parameter blocks 21a-21d. The pump 12 can reply with the requested information in block 100.

Then, in block 102, the processor 52b can compare the parameters 51a-51d and other configuration information received from the pump 12 to the parameters 51a-51d that were altered in block 96. Differences between the sets of parameters 51a-51d can be displayed on the display 58b. Then, in block 104, the computer 17b can prompt the user for confirmation of the changes. If the user decides to abort changing the configuration of the pump 12 (decision block 104 answered negatively), the method 81 can terminate. However, if the user confirms the change (decision block 104 answered affirmatively), then block 106 can follow.

In block 106, the processor 52b of the computer 17b can perform a validation of the new configuration (i.e., the processor 52b can perform a test to determine whether the pump 12 will be fully operable with the parameters 51a-51d changed in block 104). This occurs prior to actually writing the new configuration to the pump 12. Therefore, proper operations of the pump 12 can be ensured.

Assuming that the new configuration is valid, block 108 can follow. In block 108, the user can be once again prompted (e.g., on the display 58b) to affirm writing of the new configuration onto the pump 12. As shown in block 108, the user can affirm by selecting the "write configuration on pump" or other similar selection using the input device 54b. As a result, the computer 17b can once again establish communications with the pump 12 to begin writing the new configuration thereto.

Then, in block 110, the computer 17b can send commands to the processor 22 of the pump 12 to write the new configuration, and in block 112, the pump 12 can write the new configuration. In the embodiments illustrated, the pump 12 can overwrite the new configuration to the backup parameter blocks 21a'-21d', instead of the "active" parameter blocks 21a-21d. That way, the pump 12 can continue to operate during this reconfiguration with the "active" parameter blocks 21a-21d governing the operations of the pump 12 (i.e., before the new parameters 51a-51d take effect). In additional embodiments, the pump 12 can write new parameter blocks that correspond to the "active" parameter blocks 21a-21d instead of overwriting existing parameter blocks.

Also, in some embodiments of blocks 110 and 112, the pump 12 can overwrite the backup parameter blocks 21a'-21d' one-by-one (i.e., in succession). In other embodiments, the pump 12 can overwrite multiple parameter blocks 21a'-21d' substantially simultaneously. Also, the display 58b can simultaneously inform the user of the progress of overwriting.

Next, in block 114 (FIG. 6B), the processor 52b can determine whether the reconfiguration process of blocks 110 and 112 has been successfully completed. If unsuccessful (e.g., due to the process timing out, etc.), then block 116 can follow. In block 116, the computer 17b can send an "abort" command to the pump 12. As a result, the pump 12 can abort the overwriting process in block 124.

However, if the reconfiguration process of blocks 110 and 112 has been successfully completed, then block 118 can follow. In block 118, the computer 17b can send the pump 12 a command to close the reconfiguration session. As a result, the pump 12 can close the session in block 120. Next, the processor 22 of the pump 122 can perform a validation of the new configuration.

As shown, decision block 126 can follow block 122. In decision block 126, the processor 22 determines whether the new configuration is complete and otherwise valid for running the pump 12. If the new configuration is valid (block 126 answered affirmatively), then block 128 can follow. In block 128, the processor 22 can overwrite the "old" configuration contained in the "active" parameter blocks 21a-21d with the "new" configuration contained in the "backup" parameter blocks 21a'-21d'.

However, if the new configuration is incomplete or otherwise invalid (decision block 126 answered negatively), then block 130 can follow. In block 130, the "backup" parameter blocks 21a'-21d' containing the "new" configuration can be restored back to the "old" configuration by overwriting the "backup" parameter blocks 21a'-21d' with the information contained in the "active" parameter blocks 21a-21d.

Thereafter, in block 132, the pump 12 can send a current status of the pump 12 to the computer 17b. Then, in block 134, the processor 134 can report the status of the pump 12. If the pump 12 has been successfully reconfigured (block 134 answered affirmatively), then the display 58b can display a "configuration accepted" or other similar statement to the user. However, if the reconfiguration was unsuccessful (block 134 answered negatively), then the display 58b can display a "new configuration not written" or other similar statement to the user.

In additional embodiments, if the reconfiguration includes reconfiguring the language displayed on the display 58b (e.g., a change from the English language to Arabic), then the method 81 can include additional features. For instance, in blocks 86 and 100, the pump 12 can communicate to the computer 17b the language currently being used, all of the languages that are available for use on the pump 12, etc. Also, the validation performed in block 122 can include validating the new language as well a validation of the language resources on the pump 12.

Accordingly, the system 10 and methods 69, 81 described herein can allow the pump 12 to be configured by one or more independent configuring devices 15a-15c (here, the meter 19, the first computer 17a, and the second computer 17b). The parameters 51a-51d can be protected from unauthorized reconfigurations by ensuring that the configuring device 15a-15c have sufficient authorization to do so. As such, pump 12 can operate as intended.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

What is claimed is:

1. A computer-implemented method of configuring an insulin pump using a pump configuring device, the pump configuring device having a predetermined authorization level, the method comprising:
    defining a plurality of parameter blocks in a memory device of the insulin pump;
    storing a plurality of parameters and an associated restriction setting in the plurality of parameter blocks, each of the parameter blocks in the plurality of parameter blocks includes a different parameter and an associated restriction setting;
    receiving, by the pump configuring device, a request to access a given parameter on the insulin pump;
    identifying, by the pump configuring device, a given parameter block from the plurality of parameter blocks by querying the insulin pump for a memory location of the given parameter block in the memory device of the insulin pump;
    retrieving, by the pump configuring device from the insulin pump, the given parameter and the given restriction setting from the given parameter block;
    comparing, by a processor of the pump configuring device, the authorization level of the pump configuring device to the given restriction setting retrieved from the insulin pump;
    determining, by the pump configuring device, if the authorization level of the pump configuring device is greater than the given restriction setting retrieved from the insulin pump;
    performing one of:
        writing, by the pump configuring device, a new value of the given parameter to the given parameter block in response to the determination that the authorization level of the pump configuring device is greater than the given restriction setting retrieved from the insulin pump; or
        changing, by the pump configuring device, a visual attribute of the given parameter on the display in response to the determination that the authorization level of the pump configuring device is less than the given restriction setting retrieved from the insulin pump; and
    displaying, by the pump configuring device, the given parameter on a display.

2. The method of claim 1, further comprising displaying, by the pump configuring device, the given parameter on a display of the pump configuring device.

3. The method of claim 2, wherein displaying the given parameter includes displaying the given parameter as a changeable parameter in response to the determination that the pump configuring device is authorized to write to the given parameter block, and
    further comprising receiving, by the pump configuring device, a request to change the given parameter to the new value.

4. The method of claim 3, further comprising prompting a user of the pump configuring device for confirmation of the request to change the given parameter to the new value.

5. The method of claim 2, wherein displaying the given parameter includes displaying the given parameter to indicate that the given parameter is unchangeable in response to a determination that the pump configuring device is unauthorized to write to the given parameter block.

6. The method of claim 1, wherein identifying the given parameter block that stores the given parameter on the memory device of the insulin pump includes:
    requesting, by the pump configuring device from the insulin pump, a location of the given parameter block on the memory device of the insulin pump; and
    receiving, from the insulin pump to the pump configuring device, the location of the given parameter block on the memory device of the insulin pump.

7. The method of claim 1, wherein the pump configuring device is one of a first pump configuring device and a second pump configuring device, wherein the first pump configuring device has a first authorization level and the second pump configuring device has a second authorization level, wherein the second authorization level authorizes writing to more of the plurality of parameter blocks than the first authorization level.

8. The method of claim 7, wherein the first pump configuring device is a blood glucose meter and the second pump configuring device is a personal computer that runs pump configuring software.

9. The method of claim 7, wherein the first pump configuring device is the insulin pump, and the second pump configuring device is a blood glucose meter.

10. The method of claim 1, wherein the plurality of parameter blocks include a plurality of active parameter blocks and a plurality of backup parameter blocks, each of the active parameter blocks having a corresponding backup parameter block.

11. The method of claim 10, further including:
    writing the given parameter to a given backup parameter block, wherein the given backup parameter block has a corresponding given active parameter block;

determining, using the processor of the pump configuring device, whether the insulin pump is operable with the given parameter written in the given backup parameter block;

writing the given parameter to the given active parameter block if the insulin pump is operable with the given parameter; and writing the given backup parameter block with data stored in the given active parameter block if the insulin pump is not operable with the given parameter.

12. The method of claim 1, wherein writing to the given parameter block includes writing to at least two parameter blocks in succession.

13. A diabetes treatment system comprising:
an insulin pump having a plurality of parameter blocks defined in a memory therein and configured with a plurality of parameters stored in the plurality of parameter blocks, such that each of the parameter blocks in the plurality of parameter blocks includes a different parameter and an associated restriction setting;
a pump configuring device including
an input device that is operable to receive a request to access a given parameter on the insulin pump;
a memory device of the pump configuring device with a predetermined authorization level of the pump configuring device saved thereon;
a communication device that is operable to communicate with the insulin pump to retrieve the given parameter and a given restriction setting stored on a given parameter block on a memory device of the insulin pump; and
a processor that is operable to compare the authorization level of the pump configuring device to the given restriction setting and determine if the authorization level of the pump configuration device is greater than the given restriction setting, and write to the given parameter block on the insulin pump only in response to a determination that the authorization level of the pump configuring device is greater than the given restriction setting retrieved from the insulin pump.

14. The pump configuring device of claim 13, further comprising a display that is operable to display the given parameter.

15. The pump configuring device of claim 14, wherein the display is operable to display the given parameter as a changeable parameter in response to the determination that the pump configuring device is authorized to write to the given parameter block, the input device is operable to receive a request to change the given parameter to a new value, and wherein the processor is operable to write the new value of the given parameter to the given parameter block.

16. The pump configuring device of claim 14, wherein the display is operable to display the given parameter to indicate that the given parameter is unchangeable in response to a determination that the pump configuring device is unauthorized to write to the given parameter block.

17. The pump configuring device of claim 13, wherein the pump configuring device is one of a blood glucose meter and a personal computer that runs pump configuring software, wherein the blood glucose meter has a first authorization level and the computer has a second authorization level, wherein the second authorization level authorizes writing to more of the plurality of parameter blocks than the first authorization level.

18. The pump configuring device of claim 13, wherein the pump configuring device is one of the insulin pump and a blood glucose meter, wherein the insulin pump has a first authorization level and the blood glucose meter has a second authorization level, wherein the second authorization level authorizes writing to more of the plurality of parameter blocks than the first authorization level.

19. A diabetes treatment system comprising:
an insulin pump having a plurality of parameter blocks defined in a memory therein and configured with a plurality of parameters stored in the plurality of parameter blocks, each of the parameter blocks in the plurality of parameter blocks includes a different parameter and an associated restriction setting; and
an insulin pump configuring device that includes:
an input device that is operable to receive a request to access a given parameter on the insulin pump;
a memory device with a predetermined authorization level of the pump configuring device saved thereon;
a communication device that is operable to communicate with the insulin pump to retrieve the given parameter and a given restriction setting associated with the given parameter stored on a given parameter block of a memory device of the insulin pump; and
a processor that is operable to compare the authorization level of the pump configuring device to the given restriction setting and determine if the authorization level of the pump configuration device is greater than the given restriction setting, and perform one of write a new value of the given parameter to the given parameter block on the insulin pump or change a visual attribute of the given parameter on the display, wherein writing a new value of the given parameter to the given parameter block occurs in response to a determination that the authorization level of the pump configuring device is greater than the given restriction setting retrieved from the insulin pump; and
changing a visual attribute of the given parameter on the display occurs in response to a determination that the authorization level of the pump configuring device is less than the given restriction setting retrieved from the insulin pump, wherein the insulin pump is operable to administer insulin in accordance with the given parameter written to the given parameter block.

* * * * *